United States Patent [19]

Becher et al.

[11] Patent Number: 4,563,212

[45] Date of Patent: Jan. 7, 1986

[54] HIGH CONCENTRATION ENCAPSULATION BY INTERFACIAL POLYCONDENSATION

[75] Inventors: David Z. Becher, St. Louis; Ralph W. Magin, Chesterfield, both of Mo.

[73] Assignee: Monsanto Company, St. Louis, Mo.

[21] Appl. No.: 566,108

[22] Filed: Dec. 27, 1983

[51] Int. Cl.$^4$ ............................................. A01N 37/18
[52] U.S. Cl. .................... 71/118; 71/DIG. 1
[58] Field of Search .............. 71/64.11, 27, 3, DIG. 1, 71/118, 65; 264/4, 4.1, 4.7

[56] References Cited

U.S. PATENT DOCUMENTS

| | | | |
|---|---|---|---|
| 3,429,827 | 2/1969 | Ruus | 424/19 |
| 3,577,515 | 5/1971 | Vandegaer | 424/32 |
| 3,869,406 | 3/1975 | Matsukawa et al. | 264/4 |
| 4,280,833 | 7/1981 | Beestman et al. | 71/64.11 |
| 4,294,921 | 10/1981 | Yamaguchi et al. | 264/4 |
| 4,417,916 | 11/1983 | Beestman et al. | 71/64.11 |

*Primary Examiner*—Ferris H. Lander

*Attorney, Agent, or Firm*—Richard H. Shear; Patricia A. Coburn

[57] ABSTRACT

This invention relates to a process for encapsulation, and particularly to the production of small or minute capsules constituted by a skin or thin wall of polymeric material e.g., polyurea, polyamide, polysulfonamide, polyester, polycarbonate, or polyurethane, which involves first providing an aqueous solution (continuous phase liquid) containing an emulsifier selected from the group consisting of sulfonated napthalene formaldehyde condensates, sulfonated polystyrenes derivatives and functionalized oligomers. A discontinuous (immiscible or organic) phase liquid containing a water-immiscible material which is the material to be encapsulated, plus a first shell wall component; is dispersed in the aqueous liquid to form an oil-in-water emulsion. The second shell wall component is added to the oil-in-water emulsion whereupon the first shell wall component reacts with the second shell wall component to form a solid polycondensate shell wall about the material to be encapsulated. The capsules formed may be directly used as in the form of an aqueous suspension.

19 Claims, No Drawings

HIGH CONCENTRATION ENCAPSULATION BY INTERFACIAL POLYCONDENSATION

BACKGROUND OF THE INVENTION

This invention relates to a process for producing small or minute capsules containing a water-immiscible material which comprises dissolving a first shell wall component in a water-immiscible material, which is the material to be encapsulated, dispersing the resulting mixture, said mixture being the oil or discontinuous phase liquid into an aqueous phase liquid containing an emulsifier which is selected from the group consisting of sulfonated naphthalene-formaldehyde condensates, sulfonated polystyrenes and functionalized oligomers to form an oil-in-water (O/W) emulsion and thereafter adding a second shell wall component (usually dissolved in additional aqueous phase liquid) to the oil-in-water emulsion whereby the second shell wall component reacts with the first shell wall component to form a polycondensate shell wall about the water-immiscible material at the oil/water interface.

The process of microencapsulation described herein is a modification of known interfacial polycondensation techniques. Such techniques are thoroughly described in the literature, with the article entitled "Interfacial Polycondensation, a Versatile Method of Polymer Preparation" by P. W. Morgan, *Society Plastics Engineers Journal* 15, 485–495 (1959), providing a good summary of the reactions involved and the polymers which can be used in this method. The use of the technique of interfacial polymerization in a process of microencapsulation is also known; e.g., MICROCAPSULE PROCESSING AND TECHNOLOGY, Asaji Kondo, Edited by J. Wade Von Valkenburg, pp. 35–45, Marcel Dekker, Inc., New York, NY 10016 (1979). Exemplary of the patents directed to microencapsulation via interfacial polycondensation reaction are U.S. Pat. Nos. 3,429,827, 3,577,515, and 4,280,833 and British Pat. No. 1,371,179.

Microencapsulation of water-immiscible materials utilizing an interfacial polycondensation reaction generally involves the following procedure. A first reactive monomeric or polymeric material(s) (first shell wall component) is dissolved in the material to be encapsulated to form the oil or discontinuous phase liquid. The discontinuous phase liquid is dispersed into an aqueous or continuous phase liquid to form an oil-in-water (O/W) emulsion. The continuous phase (aqueous) liquid may contain a second reactive monomeric or polymeric material (second shell wall component) at the time the discontinuous phase is dispersed into the continuous phase. If this is the case, the first and shell wall components will immediately begin to react at the O/W interface to form a polycondensate shell wall about the material to be encapsulated. However, the preferred practice is to form the O/W emulsion before the second shell wall component is added to the emulsion. This enhances the formation of a stable O/W emulsion before the interfacial polycondensation reaction is initiated and prevents the formation of agglomerates.

The capsules produced in this fashion may be any desired size, for example, of the order of 1 micron up to 100 microns or larger in diameter, preferably the size of the microcapsules will range from about 1 to about 50 microns in diameter. Capsules of this character have a variety of uses, as for containing dyes, inks, chemical agents, pharmaceuticals, flavoring materials, pesticides, herbicides, and the like. Any liquid, oil, meltable solid or solvent soluble material into which the first shell wall component can be dissolved and which is nonreactive with said first shell wall component may be encapsulated with this process. Once encapsulated, the liquid or other form is preserved until it is relased by some means or instrumentality that breaks, crushes, melts, dissolves, or otherwise removes the capsule skin or until release by diffusion is effected under suitable conditions.

A method of microencapsulation bases on in situ interfacial condensation polymerization is disclosed in British Pat. No. 1,371,179. This patent discloses a process which consists of dispersing an organic pesticide phase containing a polymethylene polyphenylisocyanate or toluene diisocyanate monomer into an aqueous phase. The wall forming reaction is initiated by heating the mixture to an elevated temperature at which point the isocyanate monomers are hydrolyzed at the interface to form amines, which in turn react with unhydrolyzed isocyanate monomers to form the polyurea microcapsule wall. One difficulty with this method is the possibility of continued reaction of monomer after packaging. Unless all monomer is reacted during the preparation, there will be continued hydrolysis of the isocyanate monomer with evolution of $CO_2$, resulting in the development of pressure in the packaged formulation.

A method of encapsulation by interfacial condensation between direct-acting, complimentary reactants is disclosed in U.S. Pat. No. 3,577,515, which describes a continuous or batch method which requires a first reactant (shell wall component) and a second reactant (shell wall component) complimentary to the first reactant, with each reactant in separate phases, such that the first and second reactants react at the interface between the droplets to form encapsulated droplets. The process is applicable to a variety of polycondensation reactions, i.e., to many different pairs of reactants capable of interfacial condensation from respective carrier liquids to yield solid film at the liquid interface. The resulting capsule skin may be produced as a polyamide, polysulfonamide, polyester, polycarbonate, polyurethane, polyurea or mixtures of reactants in one or both phases so as to yield corresponding condensation copolymers. In the practice of the process described by U.S. Pat. No. 3,577,515, the liquid which preponderates becomes the continuous phase liquid. That is, in forming oil containing microcapsules, the aqueous liquid would preponderate; when water soluble materials are encapsulated, the oil phase would preponderate, i.e., become the continuous phase liquid.

Although there are a number of methods available in the art for producing microcapsules via interfacial polycondensation reactions, there are various disadvantages associated with the prior art methods. The encapsulated materials formed by the in situ interfacial polymerization process of British Pat. No. 1,371,179, require post-treatment to prevent continued carbon dioxide evolution and excessive caking, thereby increasing the costs of the finished product. The process described by U.S. Pat. No. 3,577,515, while adequate if one desires to encapsulate low concentrations of water-immiscible materials, is inadequate if concentrated amounts (i.e., greater than 480 grams/liter of water-immiscible material, is to be encapsulated in the respect that either one cannot form the necessary oil-in-water emulsion in the first instance or if microcapsules form, they cannot be maintained in discreet form since they tend to agglomerate into large unuseable masses.

U.S. Pat. No. 4,280,833 describes a process of microencapsulation via an interfacial polycondensation reaction whereby concentrated amounts of water-immiscible material, i.e., 480 grams or greater of water-immiscible material per liter of composition, is encapsulated in a polyurea shell wall with the finished capsules forming a suspension in the aqueous phase liquid. The ability to obtain high concentration microencapsulation is obtained by the use of the salts of lignin sulfonate to achieve exceptionally stable emulsions prior to the addition of the second shell wall component.

Surprisingly, it has been discovered that certain other emulsifiers, i.e., sulfonated naphthalene-formaldehyde condensates, sulfonated styrenes, and certain functionalized oligomers can be used in the process of microencapsulation via an interfacial polycondensation reaction to achieve microencapsulation of concentrated amounts of water-immiscible material(s). The present invention thus provides a new and improved encapsulation process via an interfacial polycondensation reaction which is rapid and effective to encapsulate high concentrations of water-immiscible material and which avoids the necessity of separation of the encapsulated material from the continuous, i.e., aqueous, phase liquid. Once the water-immiscible material, for example, a herbicide, is encapsulated, one has a solid in liquid suspension (i.e., a water-based flowable composition) which can be directly combined with other water-based materials, for example, pesticides or fertilizers.

The critical feature of the present invention resides in the use of the specific types of emulsifiers described herein to form a sufficiently stable oil/water emulsion so that a concentrated amount of water-immiscible material is present in the water-immiscible phase and is thereafter encapsulated. Generally, there will be greater than 480 grams of water-immiscible material per liter of total composition. By use of the specific emulsifier described herein, it is possible to retain the finished microcapsules in the original aqueous solution, thus avoiding the additional step of separation of the microcapsules from the aqueous environment. Further, the finished microcapsules do not agglomerate nor does the aqueous capsule mass solidify when stored for extended periods of time (on the order of six months or greater) or when exposed for short terms to elevated temperatures.

The invention is applicable to a large variety of polycondensation reactions, i.e., to many different pairs of reactants capable of interfacial condensation at the organic/aqueous phase interface to form microcapsules. A number of basic types of polycondensation reactions, are known and can be utilized in the present process. Thus, as examples, the resulting capsule skin or enclosure may be produced as a polyamide, polysulfonamide, polyester, polycarbonate, polyurethane, or polyurea, and the reactions of the invention may also involve mixtures of reactants in one or both phases, so as to yield corresponding condensation copolymers if desired, e.g., mixed polyamide/polyester, or polyamid/polyurea capsule shell walls.

The present invention is particularly advantageous when employed to encapsulate agricultural chemicals, as for example, herbicides, especially acetanilide and thiocarbamate herbicides like alachlor, butachlor, metolachlor, 2-chloro-N-(ethoxymethyl)-6'-ethyl-o-acetoluidide, α-chloro-N-(ethoxymethyl)-N-[2-methyl-6-(trifluoromethyl)phenyl]-acetamide, triallate, diallate, and the like. Other types of agricultural chemicals which may be advantageously encapsulated according to this invention are insecticides, fungicides, plant growth regulators, herbicidal safeners (antidotes) and the like.

Aqueous suspensions of pesticide and herbicide microcapsules are particularly useful in controlled release pesticide formulations, because they can be diluted with water or liquid fertilizer and sprayed using conventional agricultural spraying equipment, thereby producing uniform field converage of the pesticide or herbicide. Additives such as film forming agents can be added directly to the finished formulation to improve the adhesion of microcapsules to foliage. In some cases, reduced toxicity and extended activity of encapsulated herbicides and pesticides may result.

Experiments indicate that conventional oil/water herbicide emulsifiers fail to produce suitable emulsions for attaining microencapsulation of concentrated amounts of herbicide material and avoiding solidification of the oil/water mass when the second shell wall is added to the oil/water emulsion. Additionally, attempts to encapsulate concentrated amounts of acetanilide and thiocarbamate herbicides (four to five pounds per gallon) using traditional interfacial polymerization techniques, as for example that disclosed in U.S. Pat. No. 3,577,515, have resulted in unsatisfactory formulations because of the problem of rapid herbicide crystal growth in the finished suspension, as well as agglomeration or solidification of the microcapsules in the finished suspensions. The problem is particularly acute with the acetanilide herbicides. Crystal growth is undesirable because once it occurs past a certain level, the final formulations cannot be used directly; rather the microcapsules must be separated from the aqueous solution and resuspended in water before they can be sprayed in conventional agricultural herbicide and fertilizer spraying apparatus.

It is accordingly a particular object of this invention to provide a process whereby greater than 480 grams per liter of acetanilide herbicides, e.g., alachlor, propachlor, butachlor, and thiocarbamate herbicides, e.g., triallate, diallate, and the like, is encapsulated in a polymeric shell wall with the finished microcapsules being suspended in the original aqueous phase liquid.

DETAILED DESCRIPTION OF THE INVENTION

The invention relates to a process of encapsulating a water-immiscible material within a shell wall of polycondensate, e.g., polyurea, polyamide, polysulfonamide, polyester, polycarbonate, or polyurethane. The procedure of the invention involves first providing an aqueous solution containing an emulsifier selected from the group consisting of sulfonated naphthalene formaldehyde condensates, sulfonated polystyrenes and functionalized oligomers. An organic or discontinuous phase liquid which is the water-immiscible material (the material to be encapsulated) with the first shell wall component, dissolved therein is thereafter added to the aqueous phase, with agitation, to form a dispersion of small droplets of oil or discontinuous phase droplets throughout the aqueous phase; i.e., an oil-in-water emulsion is formed. Thereafter, a second shell wall component is added, with continued agitation, to the oil-in-water emulsion. The second shell wall reacts with said first shell wall component to form a shell wall about the water-immiscible material.

The water-immiscible material referred to herein is the material to be encapsulated and is suitably any liquid, oil, meltable solid or solvent soluble material, into which the first shell wall component can be dissolved and which is nonreactive thereto. Such water-immiscible materials as herbicides, e.g., α-chloro-2',6'-diethyl-N-methoxymethyl acetanilide (commonly known as alachlor), N-butoxymethyl-α-chloro-2',6'-diethylacetanilide (commonly known as butachlor), 2'-methyl-6'-ethyl-N-(1-methoxyprop-2-yl)-2-chloroacetanilide (commonly known as metolachlor), 2'-t-Butyl-2-chloro-N-methoxymethyl-6'-methylacetanilide, α-Chloro-N-(2-methoxy-6-methylphenyl)-N-(1-methylethoxymethyl)acetamide, α-Chloro-N-(ethoxymethyl)-N-[2-methyl-6-(trifluoromethyl)phenyl]-acetamide, α-Chloro-N-methyl-N-[2-methyl-6-(3-methylbutoxy)phenyl]acetamide, α-Chloro-N-methyl-N-(2-methyl-6-propoxyphenyl)acetamide, N-(2-butoxy-6-methylphenyl)-α-chloro-N-methyl acetamide, Isobutyl ester of (2,4-dichlorophenoxy)acetic acid, 2-Chloro-N-(ethoxymethyl)-6'-ethyl-o-acetotoluidide, 1-(1-cyclohexen-1-yl)-3-(2-fluorophenyl)-1-methyl urea, S-2,3,3-trichloroallyl-diisopropyl thiocarbamate (commonly known as triallate), S-2,3-dichloroallyldiisopropylthiocarbamate (commonly known as diallate), α,α,α-trifluoro-2,6-dinitro-N,N-dipropyl-p-toluidine (commonly known as trifluralin), N-(3,4-dichlorophenyl)-N'-methoxy-N'-methylurea (commonly known as linuron); insecticides, e.g., methyl and ethyl parathion, pyrethrin and pyrethroids (e.g., permethrin and fenvalerate); herbicidal safteners (antidotes), e.g., 5-thiazolecarboxylic acid, 2-chloro-4-(trifluoromethyl)-, (phenylmethyl)ester, and organic solvents, e.g., xylene and monochlorobenzene are specifically contemplated herein.

In the practice of the preferred embodiment of the present invention, the material to be encapsulated is an agricultural chemical, as, for example, a herbicide, a herbicidal saftener, plant growth regulator, insecticide, fungicide, or the like.

In utilizing the process of the present invention, the material to be encapsulated need not consist of only one type, but may be a combination of two or more various types of water-immiscible materials. For example, employing an appropriate water-immiscible material, such a combination is an active herbicide with another active herbicide or an active herbicide and an active insecticide. Also contemplated is a water-immiscible material to be encapsulated which comprises an active ingredient, such as a herbicide, and an inactive ingredient such as a solvent or adjuvant.

The water-immiscible material containing the first shell wall component dissolved therein comprises the organic or discontinuous phase liquid. The water-immiscible material acts as the solvent for the first shell wall component thus avoiding the use of other water-immiscible organic solvents and allowing for a concentrated amount of water-immiscible material in the final encapsulated product. The water-immiscible material and first shell wall component are added simultaneously to the aqueous phase in a pre-mixed state. That is, the water-immiscible material and first shell wall component are pre-mixed to obtain a homogeneous organic or discontinuous phase liquid before addition to and emulsification in the aqueous phase to form the oil-in-water emulsion.

The concentration of water-immiscible material initially present in the water-immiscible phase should be sufficient to provide at least about 480 grams of water-immiscible material per liter of total composition. However, this is by no means limiting and a greater amount can be used. In practical operation, as will be recognized by those skilled in the art, the use of extremely high concentrations of water-immiscible material will result in very thick suspensions of microcapsules. In general, the concentration of water-immiscible material will range from about 480 grams to about 700 grams per liter of total composition. The preferred range is from about 480 grams to about 600 grams per liter of total composition.

As more specific instances of polycondensation reactions to which the present encapsulation process is applicable, the following may be mentioned: diamines or polyamines in the water phase and diacid or polyacid chlorides in the organic phase liquid yield capsule walls consisting of polyamides. Diamines or polyamines in the aqueous liquid and dichloroformates or polychloroformates in the organic liquid yield a polyurethane capsule skin. Diamines or polyamines in the aqueous liquid and disulfonyl or polysulfonyl chlorides in the organic liquid produce a polysulfonamide capsule skin. Diamines or polyamines in the aqueous phase liquid and a diisocyanate or polyisocyanate in the organic phase liquid produce a polyurea skin. With diols or polyols in the aqueous liquid and diacid or polyacid chlorides in the organic phase liquid, polyester shell walls are produced. When bischloroformates or polychloroformates are used in the organic liquid, the capsule skins are polycarbonates.

It will further be appreciated that not only are there other complementary intermediates which react to form polycondensates in a direct manner useful in the interfacial condensation process of encapsulation, but various mixtures of intermediates, i.e., mixtures of shell wall components may be employed in either or both of the aqueous and organic phases. For example, mixtures of diols and diamines in the aqueous liquid and an acid chloride(s) in the organic liquid are useful to achieve polyester/polyamide condensation copolymers. Also, diamines or polyamines in the aqueous liquid and mixtures of diacid or polyacid chlorides and diisocyanates or polyisocyantes in the organic liquid produce a polyamide/polyurea skin.

Examples of suitable difunctional acid-derived shell wall components are sebacoyl chloride, ethylene bischloroformate, phosgene, terephthaloyl chloride, adipoyl chloride, azelaoyl chloride (azelaic acid chloride), dodecanedioic acid chloride, dimer acid chloride, and 1,3-benzenesulfonyl dichloride. Polyfunctional compounds of this type are exemplified by trimesoyl chloride, 1,2,4,5 benzene tetracid chloride, 1,3,5 benzene trisulfonyl chloride, trimer acid chloride, citric acid chloride, and 1,3,5 benzene trischloroformate. Intermediates similarly useful in the organic phase also include diisocyanates and polyisocyanates, for example, toluene diisocyanate, hexamethylene diisocyanate, methylene diphenylisocyanate and polymethylene polyphenylisocyanate.

As used herein, the term "first shell wall component" refers to a material or mixture of materials which is soluble in the material to be encapsulated and which is capable of reacting with the second shell wall component to form a polymeric shell wall about the material to be encapsulated. The material to be encapsulated together with the first shell wall component constitute the organic or discontinuous phase liquid.

The term "second shell wall component", as used herein, refers to a water soluble material, i.e., a material which is soluble in the aqueous phase liquid and which will react with the first shell wall component to form a polycondensate shell wall about the material to be encapsulated. The following illustrates the type of polycondensate shell wall formed when various first and second shell wall components are utilized in the process of encapsulation described herein:

| First Shell Wall Component | Second Shell Wall Component | Polymeric Shell Wall |
| --- | --- | --- |
| Diacid or Polyacid Chlorides | Diamine or Polyamine | Polyamide |
| Dichloroformates or Polychloroformates | Diamine or Polyamine | Polyurethane |
| Diisocyanates or Polyisocyanates | Diols or Polyols | Polyurethane |
| Disulfonyl or Polysulfonyl Chlorides | Diamine or Polyamine | Polysulfonamide |
| Diisocyanates or Polyisocyanate | Diamine or Polyamine | Polyurea |
| Diacid or Polyacid Chlorides | Diols or Polyols | Polyester |
| Dichloroformates or Polychloroformates | Diols or Polyols | Polycarbonate |

Examples of suitable diols for use as intermediates in an aqueous phase are bisphenol A [2,2bis-(p,p'-dihydroxy diphenyl)propane], hydroquinone, resorcinol, catechol, and various glycols such as ethylene glycol, pentanediol, hexanediol, dodecanediol, 1,4-butanediol and the like. Polyfunctional alcohols of this character, e.g., triols, are exemplified by pyrogallol(1,2,3-benzenetriol), phloroglucinol dihydrate, pentaerythritol, trimethylolpropane, 1,4,9,10-tetrahydroxyanthracene, 3,4-dihydroxyanthranol, diresorcinol and tetrahydroxyquinone.

Instances of suitable diamines and polyamines, usually selected as water soluble per se or in water soluble salt form, where such reactant is to be included in an aqueous phase, are ethylene diamine, phenylene diamine, toluene diamine, hexamethylene diamine, diethylene triamine and piperazine. Amines which are effective as polyfunctional reactants, are, e.g., 1,3,5-benzene triamine trihydrochloride, 2,4,6-triamino toluene trihydrochloride, polyethylene imine, 1,3,6 triaminonaphthalene, 3,4,5 triamino-1,2,4 triazole, melamine, and 1,4,5,8 tetramino anthraquinone. Amines which have a functionality greater than 2 but less than 3 and which may provide a degree of crosslinking in the shell wall are the polyalkylene polyamines e.g., tetraethylene pentamine, pentaethylene hexamine, and the like.

The first shell wall component and the second shell wall component form the shell wall which encapsulates the water-immiscible material. The shell wall content of the capsules formed by the present process may vary from about 5 percent to about 30 percent, preferably 8 to 20 percent and more particularly, 10 percent by weight, of the weight of the water-immiscible material.

The amount of first shell wall component and second shell wall component used in the process is determined by the percent shell wall content produced. Generally, there will be present in the reaction from about 3.5 percent to about 21.0 percent first shell wall component, and from about 1.5 percent to about 9.0 percent second whell wall component, relative to the weight of the water-immiscible material, present in the reaction.

Although a stoichiometric amount of second shell wall component has been used herein, it should be recognized that excess second shell wall component may be used without departing from the spirit or scope of the present invention.

The emulsifying agent, which is critical for use in the practice of the present invention to produce high concentration microencapsulation of concentrated amounts of water-immiscible materials, is selected from the following groups:

1. Sulfonated naphthalene-formaldehyde condensates having the formula:

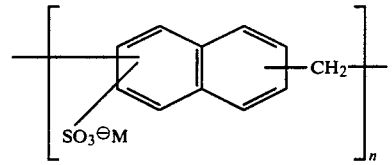

where n is 2 or 3 and M is an alkali or alkaline earth metal cation. Commercially available examples which may be mentioned are Tamol ® SN, the sodium salt of condensed naphthalene sulfonic acid manufactured by Rohm and Hass Company, Philadelphia, Pa 19105; "Daxad" 11G, 16, 17 and 19, the sodium salt of polymerized alkyl naphthalene sulfonic acid, manufactured by W. R. Grace and Company, Organic Chemicals Division, Lexington, ME 02173; "Blancol" N, the sodium salt of sulfonated naphthalene-formaldehyde condensate manufactured by GAF Corporation, Chemical Products, 140 West 51st Street, New York, NY 10020.

2. Sulfonated polystyrene polymers with molecular weights above about 1,000 and an equivalent weight per acid group between about 150 and about 750, as for example, sulfonated polystyrenes of the formula:

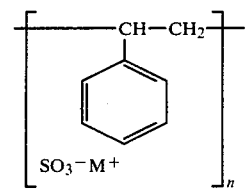

where n is greater than 5 and M is an alkali or alkaline earth metal cation.

Commercially available examples of such materials are Versa TL 500 and TL 600, sulfonated polystyrene manufactured by National Starch and Chemical Corporation, 10 Findeine Avenue, Bridgewater, N.J. 08807. Versa -TL 500 has an average molecular weight of 500,000; Versa -TL 600 has an average molecular weight of 600,000.

Functionalized oligomers are low molecular weight block co-polymers that are terminated at one end by a bulky water-insoluble group which gives the oligomer surfactant-like character. Such materials are polyionic and polymeric in nature.

Such functionalized oligomers and their preparation are described in U.S. Pat. Nos. 3,498,942, 3,498,943, 3,632,466, 3,777,382, 3,668,230, 3,776,874 and 3,839,405. Such materials are commercially available under the tradename "Polywet" and are available as the water soluble potassium, amine salts or the free acid form. The materials are manufactured by Uniroyal, Incorporated, Chemical Division, Naugatuck, CT. 96770.

The range of emulsifier concentration found most acceptable in the system will vary from about 0.5 percent to about 15 percent and preferably from about 2 percent to about 6 percent, based on the weight of the water-immiscible material and most preferably at from about 2.0 to about 4.0 percent and most preferably at a concentrate of 2 percent relative to the weight of the water-immiscible material.

The microcapsules of the present invention require no additional treatment such as separation from the aqueous liquid, but may be directly utilized or combined with, e.g., liquid fertilizers, insecticides, or the like to form aqueous solutions which may be conveniently applied in agricultural uses. Most often it is most convenient to bottle or can the aqueous suspension containing the encapsulated water-immiscible material, in which case it may be desirable to add formulation ingredients to the finished aqueous solution of microcapsules. Formulation ingredients such as density balancing agents, thickeners, biocides, surfactants, dispersants, salts, antifreeze agents, and the like can be added to improve stability and ease of application.

The process of the present invention is capable of satisfactory performance and production of encapsulated material without adjustment to specific pH value. That is, no adjustment of the pH of the system need be made during the encapsulation process. If it is desired to adjust the pH of the finished microcapsule formulation as, for example, when the aqueous solution of finished microcapsule is combined with other herbicides, pesticides, etc., conventional reagents for adjustment of acidity or alkalinity, or like characteristics may be used, such substances as hydrochloric acid, sodium hydroxide, sodium carbonate, sodium bicarbonate are commonly used by those skilled in the art.

In the practice of the process of the invention, the temperature should be maintained above the melting point of the water-immiscible material but belo the temperature wherein the polymeric shell wall will begin to hydrolyze or otherwise break down. For example, where it is desired to encapsulate a solid herbicide, it will be necessary to heat the herbicide to its molten state. Alachlor herbicide, for example, melts at 39.5° C. to 41.5° C. and the temperature of the process should accordingly be maintained above about 41.5° C.

The agitation employed to establish the dispersion of water-immiscible phase droplets in the aqueous phase may be supplied by any means capable of providing suitably high shear, that is, any variable shear mixing apparatus, e.g., a blender, a Brinkman Polytron homogenizer, Ross Model 100L homogenizer, and the like, can be usefully employed to provide the desired agitation.

The particular size of the microcapsules will range from about 1 micron up to about 100 microns in diameter. From about 1 to about 10 microns is an optimum range. From about 5 to about 50 microns is satisfactory for formulating.

The present invention will be further explained by reference to the following examples which are merely illustrative and not limiting in nature. Unless otherwise indicated, the examples which follow were prepared as follows: the water-immiscible material, containing the first shell wall component(s) dissolved therein was emulsified into water containing the emulsifier; the emulsion was formed with the aid of high shear. The second shell wall component(s), usually dissolved in an additional amount of aqueous phase liquid, was thereafter added to the emulsion and after a short period of time, the shear rate was reduced. Shear was continued for varying periods of time and thereafter salt was added to the suspension to balance the density and the formulation was bottled.

EXAMPLE 1

| Ingredient | Grams | Percent By Weight |
|---|---|---|
| Alachlor (95% tech) | 200.00 | 45.90 |
| PAPI 135 | 14.00 | 3.20 |
| 1,6-Hexamethylenediamine (42.3% aqueous solution) | 14.30 | 3.30 |
| Daxad 16 | 4.30 | 1.00 |
| Water | 163.20 | 37.40 |
| NaCl | 26.80 | 6.10 |
| CaCl$_2$ | 13.40 | 3.10 |
| | 436.00 | 100.00 |

To 200.0 grams of molten alachlor was added 14.0 grams of PAPI 135 and the mixture was stirred until all of the PAPI 135 was dissolved in the alachlor. To a Waring blender cup containing 163.2 grams of water with 4.3 grams of Daxad 16 was emulsified the alachlor/PAPI 135 mixture using high shear. High shear was continued for about 30 seconds and thereafter the shear was reduced with the concurrent addition of diamine to the emulsion, whereupon microcapsules formed; thereafter, 26.8 grams of NaCl and 13.4 grams of CaCl$_2$ was dissolved in the suspension to density balance the formulation.

Utilizing the general procedure outlined in Example 1, additional examples were prepared wherein the components were exactly the same as shown in Example 1, except that various emulsifier materials were used. Table I summarizes the various examples which were prepared.

TABLE I

| Example Number | Emulsifier | Description of Emulsifier |
|---|---|---|
| 2 | Daxad 11G | Na salt of alkylnaphthalene sulfonic acid. |
| 3 | Daxad 19 | Na salt of alkylnaphthalene sulfonic acid. |
| 4 | Blancol | Na salt of alkylnaphthalene sulfonic acid. |
| 5 | Tamol SN | Na salt of alkylnaphthalene sulfonic acid. |
| 6 | Daxad 11KLS | Potassium salt of alkylnaphthalene sulfonic acid. |
| 7 | Wettol D$_1$ | Na salt of phenol sulfonic acid condensation product. |

EXAMPLE 8

| Ingredient | Grams | Percent By Weight |
|---|---|---|
| Alachlor (92.3%) | 200.0 | 45.8 |
| PAPI 135 | 14.0 | 3.2 |
| HMD (42.3%) | 14.3 | 3.3 |
| Versa-TL 500 | 1.1 | 0.3 |
| H$_2$O | 166.4 | 38.1 |
| NaCl | 40.7 | 9.3 |
| | 436.5 | 100.0 |

This example was prepared in accordance with the procedure of Example 1. The capsules tended to agglomerate over long periods of time with resultant loss of fluidity of the suspension.

EXAMPLE 9

| Ingredient | Grams | Percent By Weight |
|---|---|---|
| Alachlor (92.3%) | 200.0 | 45.8 |
| PAPI 135 | 14.0 | 3.2 |
| HMD (42.3%) | 14.3 | 3.3 |
| Versa-TL 600 | 1.1 | 0.3 |
| H₂O | 207.1 | 47.4 |
| | 436.5 | 100.0 |

This example was prepared according to the procedure of Example 1. Excellent encapsulation was observed with the suspension showing acceptable stability with aging. The term "aging" as used herein refers to a set of three tests run to determine the shelf stability of the suspension of microcapsules; specifically, the term "aging" refers to the following: (i) storage of the sample at 50° C. for four (4) weeks; (ii) four (4) weeks cycling of the sample from 4° C. to 50° C. (one week at each temperature); (iii) storage of the suspension at room temperature for up to six (6) months.

EXAMPLE 10

| Ingredient | Grams | Percent By Weight |
|---|---|---|
| Alachlor (92.3%) | 200.0 | 46.0 |
| PAPI 135 | 14.0 | 3.2 |
| HMD (42.3%) | 14.3 | 3.3 |
| Polywet KX-4 | 10.7 | 2.5 |
| H₂O | 156.8 | 36.0 |
| NaCl | 26.1 | 6.0 |
| CaCl₂ | 13.0 | 3.0 |
| | 434.9 | 100.0 |

This example was prepared according to the procedure of Example 1. Good capsule integrity was observed; the suspension was stable after storage at 60° C. for two (2) weeks and 50° C. for four (4) weeks and also when the suspension was cycled from 4° C. to 50° C. (one week at each temperature).

In a similar fashion as was described in Example 1, the following examples may be prepared utilizing various other shell wall components and various other water-immiscible materials.

In the examples described below, when the second shell wall component is a water-sensitive monomer such as an acid chloride or chloroformate, the starting materials should be maintained at reduced temperatures, for example −5° C. to 0° C. to minimize hydrolysis of the monomer(s) by the water during the emulsion step. Higher temperatures may be employed if the pH of the aqueous phase liquid is adjusted to alter the oxidative potential of the aqueous liquid or by some other means to reduce hydrolysis of the monomers.

EXAMPLE 11

Polyurethane Shell Wall

| Ingredient | Grams |
|---|---|
| Butachlor | 200.00 |
| PAPI-135 | 14.41 |
| 1,5-Pentanediol (50%) | 11.18 |
| Daxad 16 | 4.28 |

| Ingredient | Grams |
|---|---|
| Water | 177.74 |
| NaCl | 22.04 |
| TOTAL | 429.65 |

The isocyanate (PAPI-135 ®) first shell wall component will be dissolved into butachlor. The second shell wall component, i.e., the aqueous phase monomer, 1,5-pentanediol will be added to the mixture with shear. Shear should be continued for several hours to ensure completeness of reaction. NaCl will be dissolved into the suspension and the formulation is thereafter bottled.

EXAMPLE 12

Polycarbonate Shell Wall

| Ingredient | Grams |
|---|---|
| Butachlor (95%) | 200.00 |
| Ethylene bis(chloroformate) | 12.93 |
| 1,5-Pentanediol | 12.72 |
| 1,3,5-Benzenetriol | 1.41 |
| NaOH (50%) | 11.06 |
| Water | 7.07 |
| Daxad 11G | 4.26 |
| Water | 172.00 |
| NaCl | 13.99 |
| TOTAL | 435.44 |

Ethylene bis(chloroformate) will be dissolved into molten butachlor; this mixture will become the organic or discontinuous phase liquid. The continuous phase may be prepared as follows: Daxad 11G is dissolved in the water in a Waring blender, thereafter the organic phase liquid, (i.e., mixture of butachlor/ethylene bis(chloroformate) may be emulsified into the aqueous phase liquid using high shear. Once the emulsion forms, the second shell wall components, i.e., 1,5-pentanediol and 1,3,5-benzenetriol, which will be dissolved in water and 50% NaOH (NaOH will be added to neutralize liberated chloride ion) will be added to form a polycarbonate shell wall about the butachlor. One would expect to obtain microcapsules in the range of from about 4 to about 20 microns in diameter.

EXAMPLE 13

Polyester Shell Wall

| Ingredient | Grams |
|---|---|
| Butachlor (95%) | 200.00 |
| Adipoyl chloride | 12.84 |
| 1,5-Pentanediol | 6.46 |
| 1,3,5-Benzenetriol | 0.71 |
| NaOH (50%) | 11.23 |
| Water | 7.17 |
| Versa-TL 600 | 4.26 |
| Water | 171.84 |
| NaCl | 13.87 |
| TOTAL | 428.38 |

EXAMPLE 14

Polyamide Shell Wall

| Ingredient | Grams |
|---|---|
| Butachlor (95%) | 200.00 |

| Ingredient | Grams |
| --- | --- |
| Adipoyl chloride | 6.07 |
| Trimesoyl chloride | 6.08 |
| HMDA (50%) | 15.69 |
| NaOH (50%) | 10.80 |
| Polywet KX-4 | 4.24 |
| Water | 171.32 |
| NaCl | 14.18 |
| TOTAL | 428.34 |

In this example, adipoyl chloride and trimesoyl chloride are the first shell wall components and will be dissolved in butachlor which is the material to be encapsulated. HMDA is the second shell wall component.

EXAMPLE 15

Polysulfonamide Shell Wall

| Ingredient | Grams |
| --- | --- |
| Butachlor (95%) | 200.00 |
| Benzene Disulfonyl Chloride | 9.29 |
| Benzene Trisulfonyl Chloride | 4.64 |
| HMDA (50%) | 12.15 |
| NaOH (50%) | 8.36 |
| Polywet AX-4 | 4.28 |
| Water | 174.05 |
| NaCl | 15.94 |
| TOTAL | 428.71 |

EXAMPLE 16

Mixed Polyurea/Polyamide Shell Wall

| Ingredient | Grams |
| --- | --- |
| Butachlor (95%) | 200.00 |
| Adipoyl chloride | 3.00 |
| Trimesoyl chloride | 3.00 |
| PAPI-135 ® | 7.00 |
| 1,6-Hexamethylene Diamine (50%) | 15.00 |
| NaOH (50%) | 5.77 |
| Versa-TL 600 | 4.26 |
| Water | 174.33 |
| NaCl | 17.84 |
| TOTAL | 430.20 |

In addition to the previously described advantages of the present invention, microencapsuation of agricultural chemicals like herbicides, insecticides, fungicides, plant growth regulants, and the like may, in general, offer several advantages over conventional formulations. Thus, for example, microencapsulated herbicide formulations may reduce mammalian toxicity and extend the activity of the herbicide. Where volatility of the herbicide is a problem, microencapsulation can reduce evaporative losses and thus prevent reduction in herbicide activity associated with such losses. Microencapsulated herbicide formulations may, in some cases, be less phytotoxic to certain crop plants, thereby enhancing the crop safety of the herbicide and may also protect the herbicides from environmental degradation, reduce leaching of the herbicide into the soil, and thus prolong or increase the soil life of the herbicide. It can be appreciated that microencapsulated agricultural chemical formulations have several advantages which make such microencapsulated formulations a desirable and beneficial alternative to conventional agricultural chemical formulations.

A particular object of the present invention is to provide an agricultural chemical composition consisting essentially of a suspension in water or microcapsules comprised of an agricultural chemical, especially a herbicide contained within an encapsulating wall of condensation polymer. Herbicides of the type previously described are expressly contemplated for use in such compositions, preferably the acetanilide and thiocarbamate type herbicides and particularly alachlor, butachlor, and triallate. The concentration of agricultural chemical present in such compositions will be about 480 grams per liter of aqueous suspension or greater, preferably from about 480 grams to about 700 grams per liter of aqueous suspension and more preferably, from about 480 grams to about 600 grams per liter of total composition.

It is to be understood that the present invention is not limited to the specific embodiments shown and described herein, but may be carried out in other ways without departure from its spirit or scope.

We claim:

1. A composition consisting essentially of microcapsules suspended in an aqueous liquid comprised of a water-immiscible material contained within an encapsulating wall of polymeric material wherein:
   (a) the concentration of said water-immiscible material is from about 480 grams to about 700 grams per liter of composition;
   (b) wherein said encapsulating wall of polymeric material is the reaction product of a first shell wall component which is a difunctional or polyfunctional reactant that is soluble in said water-immiscible material and a second shell wall component which is water soluble and which is a difunctional or polyfunctional reactant and wherein concentration of first shell wall component is from about 3.5% to about 21.0% relative to the weight of said water-immiscible material and wherein the concentration of said second shell wall component is from about 1.5% to about 9.0% relative to the weight of said water-immiscible material; and
   (c) wherein said water contains from about 0.5% to about 15% of an emulsifier relative to the weight of said water-immiscible material, said emulsifier being selected from the group consisting of sulfonated naphthalene formaldehyde condensates and sulfonated polystyrenes.

2. A composition as described in claim 1 wherein said polymeric shell wall is polyurea.

3. A composition as described in claim 1 wherein the concentration of said water-immiscible material is from about 480 grams to about 600 grams per liter of composition, wherein the concentration of said first shell wall component is from about 5.0% to about 14.0% relative to the weight of said water-immiscible material, wherein the concentration of said second shell wall component is from about 2.0% to about 6.0% relative to the weight of said water-immiscible material, and wherein the concentration of said emulsifier is from about 2.0% to about 6.0% relative to the weight of said water-immiscible material.

4. A composition as described in claim 3 wherein the concentration of said first shell wall component is from about 7.0% relative to the weight of said water-immiscible material, wherein the concentration of said second shell wall component is from about 3.0% relative to the weight of said water-immiscible material and wherein the concentration of said emulsifier is about 2% relative to the weight of said water-immiscible material.

5. A composition as described in claim 1 wherein said water-immiscible material is an herbicide, insecticide, plant growth regulant or an herbicidal antidote.

6. A composition as described in claim 5 wherein said herbicide is selected from the group consisting of alachlor, butachlor, triallate and diallate.

7. A composition as described in claim 1 wherein the average particle size of the microcapsules is in the range of from about 1 micron to about 50 microns in diameter.

8. A composition according to claim 1 wherein aqueous liquid additionally contains from 1% to 10% of formulation ingredients based on the weight of the total composition.

9. A process of encapsulating water-immiscible material within a shell wall of polymeric material which comprises:
(a) providing an aqueous phase containing an emulsifier selected from the group consisting of sulfonated naphthalene formaldehyde condensates and sulfonated polystyrenes;
(b) dispersing in said aqueous phase, a water-immiscible phase consisting essentially of a first shell wall component dissolved in said water-immiscible material, to form a dispersion of water-immiscible phase droplets throughout the aqueous phase;
(c) adding, with agitation, to said dispersion a second shell wall component whereby said second shell wall component reacts with said first shell wall component to form a polymeric shell wall about said water-immiscible material;
wherein the concentration of said water-immiscible material is from about 480 grams to about 700 grams per liter of composition, wherein the concentration of said emulsifier is from about 0.5% to about 15.0% by weight of said water-immiscible material, wherein the concentration of said first shell wall component is from about 3.5% to about 21.0% by weight of said water-immiscible material and wherein the concentration of said second shell wall component is from about 1.5% to about 9.0% by weight of said water-immiscible material.

10. A process according to claim 9 wherein said polymeric shell wall is selected from the group consisting of polyamide, polyurethane, polysulfonamide, polyurea, polyester and polycarbonate or mixtures thereof.

11. A process according to claim 9 wherein said polymeric shell wall is polyurea.

12. A process according to claim 11 wherein said first shell wall component is a polyisocyanate and wherein said second shell wall component is a difunctional or polyfunctional amine.

13. A process according to claim 11 wherein said first shell wall component is a diisocyanate and said second shell wall component is a polyfunctional amine or a mixture of polyfunctional and difunctional amines.

14. A process according to claim 9 wherein the concentration of said water-immiscible material is from about 480 grams to about 600 grams per liter of composition and wherein the concentration of emulsifier is from about 2.0% to about 4.0% by weight of said water-immiscible material.

15. A process according to claim 9 wherein the average particle size of the microcapsules produced by said process is in the range of from about 1 micron to about 50 microns in diameter.

16. A process according to claim 9 wherein said first shell wall component is a difunctional or polyfunctional reactant which is soluble in said water-immiscible material and which is capable of reacting with said second shell wall component to form a polymeric shell wall about said water-immiscible material.

17. A process according to claim 9 wherein said second shell wall component is a water soluble material which is capable of reacting with said first shell wall component to form a polymeric shell wall about said water-immiscible material.

18. A composition consisting essentially of a mixture of water and microcapsules containing a water-immiscible material, said mixture being produced by a process which comprises the steps of:
(a) providing an aqueous phase containing an emulsifier selected from the group consisting of sulfonated naphthalene formaldehyde condensates, sulfonated polystyrenes and functionalized oligomers;
(b) dispersing in said aqueous phase, a water-immiscible phase consisting essentially of a first shell wall component dissolved in said water-immiscible material, to form a dispersion of water-immiscible phase droplets throughout the aqueous phase;
(c) adding, with agitation, to said dispersion a second shell wall component whereby said second shell wall component reacts with said first shell wall component to form a polymeric shell wall about said water-immiscible material;
(d) wherein the concentration of said water-immiscible material is from about 480 grams to about 700 grams per liter of said composition, wherein the concentration of first shell wall component is from about 3.5% to about 21.0% by weight of said water-immiscible material, wherein the concentration of said second shell wall component is from about 1.5% to about 9.0% by weight of said water-immiscible material, and wherein the concentration of said emulsifier is from about 0.5% to about 15% by weight of said water-immiscible material.

19. A composition as described in claim 18 wherein the concentration of first shell wall component is about 7.0% relative to the weight of said water-immiscible material wherein the concentration of said second shell wall component is about 3.0% relative to the weight of said water-immiscible material and wherein the concentration of said emulsifier is about 2% relative to the weight of said water-immiscible material.

* * * * *

UNITED STATES PATENT AND TRADEMARK OFFICE
CERTIFICATE OF CORRECTION

PATENT NO. : 4,563,212

DATED : January 7, 1986

INVENTOR(S) : David Z. Becher and Ralph W. Magin

It is certified that error appears in the above-identified patent and that said Letters Patent is hereby corrected as shown below:

Claim 18, column 16, lines 27-28 should read as follows:

"sulfonated naphthalene formaldehyde condensates and sulfonated polystyrenes."

Signed and Sealed this

Fifth Day of August 1986

[SEAL]

Attest:

DONALD J. QUIGG

Attesting Officer

Commissioner of Patents and Trademarks